(12) United States Patent
Sima et al.

(10) Patent No.: US 12,297,889 B2
(45) Date of Patent: May 13, 2025

(54) ACTUATOR AND HEAT STORE FOR ACTUATOR

(71) Applicant: Otto Bock Healthcare Products GmbH, Vienna (AT)

(72) Inventors: Harald Sima, Herzogenburg (AT); Juan Pablo Mejia Nino, Mödling (AT); Joachim Haglage, Rohrau (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 360 days.

(21) Appl. No.: 17/622,671

(22) PCT Filed: Jul. 7, 2020

(86) PCT No.: PCT/EP2020/069118
§ 371 (c)(1),
(2) Date: Dec. 23, 2021

(87) PCT Pub. No.: WO2021/005056
PCT Pub. Date: Jan. 14, 2021

(65) Prior Publication Data
US 2022/0252130 A1   Aug. 11, 2022

(30) Foreign Application Priority Data
Jul. 8, 2019   (DE) ..................... 10 2019 118 422.3

(51) Int. Cl.
*F16F 9/42*      (2006.01)
*A61F 5/01*      (2006.01)
(Continued)

(52) U.S. Cl.
CPC .............. *F16F 9/42* (2013.01); *A61F 5/0102* (2013.01); *F15B 21/008* (2013.01); *F16F 9/19* (2013.01);
(Continued)

(58) Field of Classification Search
CPC ........ F16F 9/35; F16F 9/36; F16F 9/42; F16F 9/44; F16F 9/46; F16F 9/19;
(Continued)

(56) References Cited

U.S. PATENT DOCUMENTS 2,191,246 A * 2/1940 Andersen ................. B61L 5/00
                                                       188/322.21
3,795,291 A * 3/1974 Naito ....................... F16F 9/18
                                                       188/274
(Continued)

FOREIGN PATENT DOCUMENTS

DE   102011055014 A1   5/2013
DE   102014011373 A1   8/2014
(Continued)

OTHER PUBLICATIONS

"International Search Report and Written Opinion of the International Searching Authority," issued in connection with Int'l Appl. No. PCT/EP2020/069118, dated Oct. 21, 2020 (16 pages).

(Continued)

*Primary Examiner* — Christopher P Schwartz
(74) *Attorney, Agent, or Firm* — Holland & Hart LLP

(57) ABSTRACT

The invention relates to an actuator for an orthopedic device with an actuator housing and a heat store for storing the heat produced during operation of the actuator, the heat store having a heat store housing that has a cavity and a heat storage medium present therein, or consisting of a heat storage medium. The heat store is designed to be attachable to or in the actuator housing and has a receiving region that matches an actuator housing region and, when the heat store is mounted, is in heat-transferring contact with the actuator housing.

20 Claims, 4 Drawing Sheets

(51) Int. Cl.
*F15B 21/00* (2006.01)
*F16F 9/19* (2006.01)

(52) U.S. Cl.
CPC ..... *F16F 2222/025* (2013.01); *F16F 2222/12* (2013.01)

(58) Field of Classification Search
CPC ... F16F 2222/12; F16F 2222/025; A61F 2/64; A61F 5/0102; F15B 21/008
USPC ......................................................... 188/274
See application file for complete search history.

(56) References Cited

U.S. PATENT DOCUMENTS

| | | | | |
|---|---|---|---|---|
| 4,595,179 | A * | 6/1986 | Glabiszewski | A61F 2/64 188/274 |
| 5,375,683 | A * | 12/1994 | Huang | F16F 9/096 188/266.8 |
| 5,443,521 | A * | 8/1995 | Knoth | A61F 2/68 623/44 |
| 9,358,138 | B2 | 6/2016 | Kelley et al. | |
| 9,498,354 | B2 | 11/2016 | Cook | |
| 9,803,713 | B2 * | 10/2017 | Schmidt | F16F 9/325 |
| 9,814,607 | B2 | 11/2017 | Zhe et al. | |
| 11,466,746 | B2 * | 10/2022 | Schel | F16F 9/19 |
| 2010/0274364 | A1 * | 10/2010 | Pacanowsky | A61F 2/80 600/595 |
| 2012/0109041 | A1 | 5/2012 | Munz | |
| 2012/0186923 | A1 * | 7/2012 | Buma | F16F 9/006 188/268 |
| 2012/0222927 | A1 * | 9/2012 | Marking | B60G 17/08 188/274 |
| 2013/0103125 | A1 | 4/2013 | Radspieler et al. | |
| 2013/0245524 | A1 | 9/2013 | Schofield | |
| 2013/0274896 | A1 | 10/2013 | Wang et al. | |
| 2017/0202687 | A1 | 7/2017 | Anhalt et al. | |
| 2018/0058429 | A1 | 3/2018 | Kwon et al. | |
| 2018/0098864 | A1 * | 4/2018 | Auberger | A61F 2/64 |

FOREIGN PATENT DOCUMENTS

| | | |
|---|---|---|
| DE | 10 2014 011 374 A1 | 2/2016 |
| DE | 10 2017 131 195 A1 | 6/2019 |
| EP | 2568935 A2 | 3/2013 |
| JP | S-48-37572 A | 6/1973 |
| JP | 11-182393 A | 7/1999 |
| JP | 2015-178939 A | 10/2015 |
| JP | 2017-053528 A | 3/2017 |
| KR | 101691765 B1 | 12/2016 |
| RU | 2393752 C2 | 7/2010 |
| RU | 2546493 C2 | 5/2013 |
| RU | 2561834 C2 | 6/2014 |
| RU | 2401090 C1 | 10/2017 |
| WO | 2010/005473 A1 | 1/2010 |
| WO | WO 20100012822 A2 | 2/2010 |
| WO | 2010/27968 A2 | 3/2010 |
| WO | WO 2016002044 A1 | 2/2016 |

OTHER PUBLICATIONS

International Search Report and Written Opinion issued in PCT/EP2020/065687, published Jan. 14, 2021, 11 pgs.

Japan Patent Office "Decision to Grant", issued in connection with Japan Patent Application No. 20211576715. dated Jun. 18, 2024 (5 pages) (2 pages of English Translation and 3 pages Original Document).

Japan Patent Office, "JP Search report," issued in connection with Japan Patent Application No. 2021-576715 dated Dec. 5, 2023 (18 pages).

Japan Patent Office, "Office Action," issued in connection with Japan Patent Application No. 2021-576715 dated Jan. 23, 2024 (6 pages).

\* cited by examiner

ACTUATOR AND HEAT STORE FOR ACTUATOR

CROSS-REFERENCE TO RELATED APPLICATIONS

This is a national phase application of International Application No. PCT/EP2020/069118, filed 7 Jul. 2020, which claims the benefit of German Patent Application No. 10 2019 118 422.3, filed 8 Jul. 2019, the disclosures of which are incorporated herein, in their entireties, by this reference.

TECHNICAL FIELD

The invention relates to an actuator for an orthopedic device having an actuator housing and a heat store for storing the heat produced during operation of the actuator, wherein the heat store has a heat store housing with a cavity and a heat storage medium present therein. The invention likewise relates to a heat store for fastening on such an actuator.

BACKGROUND

In the cases of orthopedic devices, such as prostheses, orthoses or exoskeletons, a multiplicity of actuators is used, e.g. passive actuators such as hydraulic dampers or pneumatic dampers, or active actuators, such as electric-motor drives, pumps or the like. Active actuators, such as electric motors, can also be used together with passive actuators in order, for example, to adjust valves within a pneumatic damper or hydraulic damper to change damper properties as a function of sensor data.

In all orthopedic devices, the space required and the weight of the technical components are a decisive factor. The basic aim is to keep all additional devices attached to the body of the patient as small as possible and as light as possible in order to provide the user with the lowest possible additional weight and to cause the least possible impairment in terms of appearance. Therefore, the actuators, such as hydraulic dampers or motors, are designed to be as small and light as possible. Conversely, this means that the heat storage capacity of the components is comparatively low.

Especially when the orthopedic components are operated at their limits, the components heat up very severely since the heat storage capacity is low on account of the desired lightweight construction, and mechanical or electrical energy is dissipated in the form of heat.

SUMMARY

It is therefore the object of the present invention to provide an actuator by means of which longer operating times are possible at higher loads or in the limit range, without ignoring the aim of lightweight construction and a small space requirement.

According to the invention, this object is achieved by an actuator having the features of the main claim and a heat store having the features of the additional independent claim. Advantageous embodiments and developments of the invention are disclosed in the dependent claims, the description and the figures.

The actuator for an orthopedic device having an actuator housing and a heat store for storing the heat produced during operation of the actuator, wherein the heat store has a heat store housing, which has a cavity and a heat storage medium present therein, or consists of the heat storage medium, provides that the heat store or heat store housing is designed in such a way that it can be fixed on or in the actuator and has a receiving region, which is designed to correspond to an actuator housing section and which, in the installed state of the heat store, is in heat-transferring contact with the actuator housing. The heat store is, in particular, formed separately from the actuator housing and can be repeatedly fastened on the actuator housing and removed therefrom. By means of the heat store arranged on the actuator housing, it is possible to increase the thermal capacity of the actuator. An increased thermal capacity delays the rise of the operating temperature beyond a limit or slows the heating up of the hydraulics. Conversely, an increased heat storage capacity slows down cooling, and the peaks in the dissipative power of the actuator are smoothed. Increasing the heat storage capacity does not make it possible to lower the steady state temperature of the actuator; a cooling system would be necessary for this purpose. On the other hand, however, an increase in the heat storage capacity by means of a heat store has the advantage that, in respect of external boundary conditions that can be influenced by the user, such as clothing for the user or cladding of the orthopedic devices, the device can have an effect on the mode of operation. By configuring the heat store housing as a hollow body filled with the heat storage medium, it is possible to adapt the respective properties with regard to the quantity of heat to be stored and weight to the respective construction or else to the respective application. Thus, it is possible, for example, to introduce into the cavity a heat storage medium having a very good, specific heat capacity, wherein the heat storage medium requires less mass and volume, in comparison with the materials used for the rest of the actuator, to achieve the same heating behavior as when materials which have a higher mass and volume are used. It is likewise possible and envisaged in addition or as an alternative for the heat store to consist of the heat storage medium, being formed at least partially therefrom. The heat store is then of at least partially solid design, or the walls of the heat store housing are formed from the heat storage medium. This makes the actuator lighter and it is possible to design the actual actuator with, for example, a housing made of metal, a hydraulic cylinder and the mechanisms and drives arranged thereon in a manner which is optimized with regard to the strength and operating properties thereof, without having to take into account the necessary heat storage capacity. The respective necessary heat storage capacity is provided by means of the heat store with the heat storage medium and/or the heat store housing with the heat storage medium arranged therein, which can be minimized in terms of weight and can be maximized in terms of heat storage capacity. By functionally separating the actuator from the heat store and by assigning the mechanical and dynamic requirements to the actuator and the heat storage requirements to the heat store, it is possible to optimize the separated components separately and thus to provide an overall system which is optimized both in terms of mechanics and in terms of heat storage capacity.

A further development of the invention envisages that the heat store, in particular the heat store housing, is fastened nonpositively and/or positively on the actuator housing. The heat store, in particular the heat store housing, is fixed and secured on the actuator housing, in particular detachably and exchangeably, in order to be able to perform subsequent fastening and an increase or adaptation of the heat storage capacity to the respective conditions of use. If necessary, the heat store or the heat store housing can be removed and exchanged or replaced by a heat store, in particular a heat store with a housing or a heat store of different dimensions formed from the heat storage material.

Fastening devices, by means of which it is possible to connect the heat store, in particular the heat store housing, to the actuator housing, can be arranged or formed on the heat store, in particular the heat store housing and the actuator housing. The fastening devices are designed, in particular, as screw sockets, undercuts, clips, clamping elements, plugs, plug receptacles, magnets, ferromagnetic elements and/or hook-and-loop fastening elements. The heat store or the heat store housing can also be accommodated in the actuator housing, for example clamped or pushed into a recess. A conventional screw connection permits repeated, technically proven and reliable fastening of the heat store or heat store housing on the actuator housing. It is likewise possible to carry out reversible fixing on the actuator housing by means of clips and undercuts or other positive engagement elements, which can also be mounted or designed in a resilient manner. Plug-in closures can be provided alone or in combination with nonpositive fixing means such as magnets, ferromagnetic elements or even vacuum devices. In addition, hook-and-loop fastening elements, such as hook areas and fleece areas or similar interlocking systems, are possible, which enable the heat store housing to be fixed and preloaded in the direction of the actuator housing by means of flexible and, if appropriate, elastic devices. The ferromagnetic and/or magnetic components can be designed either as a functional part of the respective housing or as separate devices fixed on the respective housing. It is likewise possible to integrate the heat store into the actuator housing, for example to insert it into dovetail grooves, to insert it into jacketed receptacles or to design it as a preferably removable part of the actuator housing.

A further development of the invention envisages that positive engagement elements are arranged or formed on a side of the receiving region which faces the actuator, said positive engagement elements being designed to correspond to positive engagement elements on an outer side of the actuator, in order to make possible long-term, releasable and secure locking and fixing of the two housings or of the heat store and of the actuator housing to one another.

The heat store or the heat store housing can be designed to be at least partially flexible on the side of the receiving region which faces the actuator, thereby making it possible to provide the fullest possible contact in the receiving region on the outer side of the actuator housing. This ensures the greatest possible surface area and the most intensive possible contact between the housing surfaces or contact surfaces in order to allow the fastest possible heat exchange.

A further development of the invention envisages that the heat store or the heat store housing is designed to be at least partially rigid on a side which faces away from the actuator, in order to produce sufficient stability and mechanical stiffness. This makes it possible for the heat store or the heat store housing also to perform a protective function for the actuator housing. In addition, the dimensionally stable outer shell of the heat store housing or the heat store as such can provide sufficient mechanical stability for fastening the heat store housing or the heat store on the actuator housing.

The heat store and/or the heat store housing may be formed from different materials, wherein the material in the receiving region has a thermal conductivity which is higher than the thermal conductivity of the second material outside the receiving region. As a result, the heat can be transferred rapidly from the actuator into the heat store and vice versa, whereas heat is released from the heat store to the environment only at a reduced rate, with the result that heating, e.g. of an actuator of an orthosis, results only slowly in perceptible heating on the outer side of the heat store.

The outer contour and surface can be designed in such a way that optimum heat dissipation to the environment is possible. The outer contour of the side of the heat store or heat store housing which faces away from the actuator and/or the contour of the receiving region can have a contour which is designed to correspond to the contour of the outer side of the actuator. The inner side or the receiving region thus have a contour which is designed to correspond to the contour of the outer side of the actuator housing, with the result that the heat store rests as completely as possible against the outer side of the actuator housing. By means of a corresponding configuration of the outer side of the heat store housing with respect to the outer side of the actuator housing, the heat store or the heat store housing can be made to continue the actuator housing in terms of shape and appearance, resulting in an improved overall aesthetic impression here. The corresponding configuration between the inner side of the receiving region and the outer side of the actuator housing is functionally important for good heat transfer.

The actuator is preferably designed as a hydraulic actuator, in particular as a hydraulic damper; other configurations of the actuator are possible, for example as a pneumatic actuator or electric motor.

The heat store or the heat store housing can surround the actuator housing circumferentially, in particular completely. If the actuator housing has a cylindrical or substantially cylindrical outer contour, the heat store or the heat store housing is advantageously equipped with a receiving region which is designed to be cylindrical or at least partially cylindrical.

The heat store or the heat store housing can be of multi-part design, thus allowing modular construction of the heat store or the heat store housing in order to enable the heat storage capacity to be adapted to the respective requirements. A basic module of a heat store or heat store housing can be designed to be expandable by fixing further parts of the heat store housing thereon, these being fastened positively thereon or fastened detachably by pivoting into an undercut, for example. There are likewise other fastening possibilities.

The heat storage medium can have a specific heat capacity of at least 1 J/(g*K) at a temperature of 25° C. and/or a specific enthalpy of fusion of 100 kJ/kg. When configured as a filling, the heat storage medium can preferably have a lower density than the material of the heat store housing, in particular a lower density than the actuator. If the heat storage medium has a high density, a high heat storage capacity in a small installation space is generally made available, and therefore it is possible to achieve a compact design for the same amount of heat that can be stored in the heat storage medium. The heat storage medium is preferably in the form of a wax, in particular beeswax, paraffin or some other medium with corresponding properties. The heat storage medium and thus also the heat store can be in the form of a salt, salt hydrate, metastable salt hydrate, in particular sodium acetate trihydrate, or a dimensionally stable silica gel.

The heat storage medium can be designed to be actively triggerable, for example by means of a mechanical pulse or a pressure wave, with which recrystallization is triggered in order to be able to release the stored heat at a freely selectable time.

The invention likewise relates to an orthopedic device having an actuator and a heat store of the kind described above. The invention likewise relates to a heat store having a heat store housing of the kind described above. The heat store is used for attachment to an actuator of an orthopedic device of the kind described above. The configuration of the heat storage medium as a wax has, in addition to a comparatively high specific heat capacity and a low melting point of, for example, about 55° C. for beeswax, the advantages that wax does not have a corrosive effect, is electrically non-conductive and stable to cycles and, in addition, has good sound-absorbing properties. The customary temperature range in which an actuator operates leads neither to evaporation nor to freezing of the wax, leading to high operational reliability. Moreover, the melting point of beeswax, at 55° C., is advantageous in that, to further increase the temperature of the wax, the wax has to be melted, for which purpose an enthalpy of fusion of 176 kJ/kg is necessary, resulting overall in an increase in the specific heat capacity. The already high specific heat capacity of wax, in particular beeswax, is further increased by utilizing the phase transition and the enthalpy of fusion required for this, thus enabling the heat capacity of an average hydraulic actuator to be achieved with only one eighth to one ninth the mass of beeswax.

BRIEF DESCRIPTION OF THE DRAWINGS

An exemplary embodiment of the invention is explained in greater detail below with reference to the appended figures. Of the figures.

DETAILED DESCRIPTION

Figure 1:
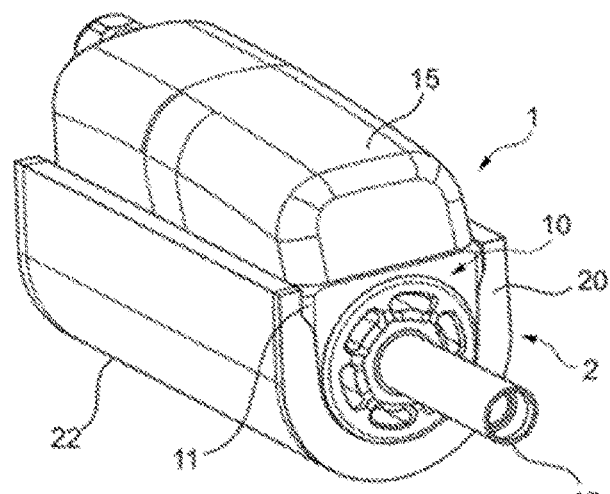
FIG. 1—shows an isometric view of a hydraulic actuator with a heat store housing arranged thereon.

In FIG. 1, in a perspective view, there is an actuator 1 in the form of a hydraulic damper having an actuator housing 10, in which a cylinder is formed, in which a piston (not visible) can be coupled to an orthopedic device via a piston rod 12. The hydraulic actuator 1 can be designed either as a hydraulic damper or as an active drive. Arranged on the actuator housing 10 is an attachment 15, in which an energy store, e.g. an accumulator, a motor drive for driving a pump or for adjusting one or more valves or the like, can be arranged. In addition, sensors, microprocessors as part of a control device and the like can be accommodated in the attachment 15; alternatively, the drive with all other components can be arranged in the actuator housing 10.

A heat store 2 with a heat store housing 20, in which a heat storage medium is located, is arranged outside the actuator housing 10. The heat store housing 20 has an outer wall 22, which consists of a rigid, dimensionally stable material, e.g. a light metal. On the inner side of the heat store housing 20, which faces the actuator housing 10, a receiving region 21 is formed which is designed to correspond to an actuator housing section 11 on the outer side of the actuator housing 10. The part of the heat store 2 which is intended to absorb heat and, if appropriate, to pass it on to the heat storage medium 26 is arranged on the receiving region 21 of the actuator housing 10. In the exemplary embodiment illustrated, the actuator housing section 11 extends from the ends of the actuator housing 10 over the entire length of the outer side of the actuator housing 10 up to the attachment 15. The piston rod 12 projects from one, visible, end of the actuator housing 10. The opposite end is provided, for example, with a fastening device for fixing on an orthopedic device, e.g. a prosthesis, orthosis or an exoskeleton.

Figure 2:
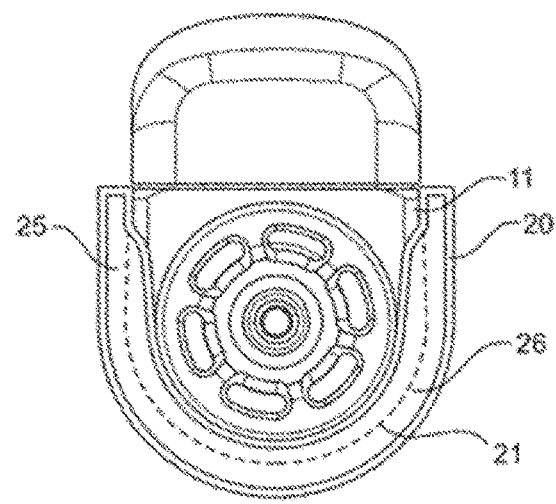
FIG. 2—shows a front view of the hydraulic actuator according to FIG. 1 with an open heat store housing.

In FIG. 2, in a frontal view with a partially sectioned heat store housing 20, the receiving region 21 can be seen, which is represented by a dashed line. The receiving region 21 rests against the actuator housing section 11 on the outer side of the actuator housing 10. As a result, the heat emitted by the actuator housing 10 can be dissipated through the receiving region 21 into the cavity 25 containing the heat storage medium 26. The heat storage medium 26, e.g. wax, stores the heat and smoothes dissipation peaks, and makes possible extended operation of the actuator 1 at high loads, with a comparatively low weight by virtue of the hollow configuration of the heat store 20 and the choice of material for the heat storage medium 26, which is adapted to the function.

A heat conductor 40, for example a thermal paste, a heat-conducting mat and/or a heat-conducting plate made of a material which is a particularly good conductor of heat, can be arranged between the actuator housing section 11 and the receiving region 21. Free spaces between the outer side of the actuator housing 10 and the receiving region 21 can be compensated for by means of the heat conductor 40.

At the transition to the attachment 15, the heat store housing 20 can have inwardly directed projections which extend into a gap or into a slot between the attachment 15 and the actuator housing 10 in order in this way to be able to perform positive locking on the actuator housing 10. For this purpose, either only the projections or the entire heat store housing 20 can be designed to be elastically expandable, thus enabling the actuator housing 10 to be placed in the receiving region, pushed in and fixed thereon by resilient positive locking. Alternatively, positive engagement elements, such as springs, plugs or, alternatively, screw connections, can be provided and arranged or formed on the actuator housing 10 and the heat store housing 20 in order to be able to perform detachable and, advantageously, reusable fastening of the heat store 2 on the actuator housing 10. Permanent connection is possible, e.g. by means of an adhesive bond, for example by means of an adhesive heat conductor. As an alternative or in addition, a nonpositive connection can be produced by means of magnetic coupling.

Figure 3:
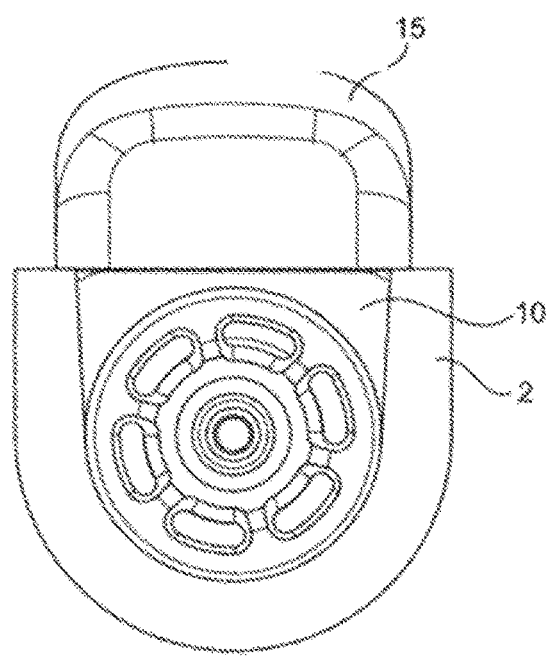
FIG. 3—shows a variant of FIG. 2.

FIG. 3 shows a variant of the invention according to FIG. 2, in which, instead of a hollow body with a filling comprising a heat storage medium 26, the heat store 2 is formed from the heat storage medium 26. The heat storage medium 26 of the heat store 2 is preferably a material with a very high heat absorption capacity, e.g. a silica gel, which is applied directly to the actuator housing 10 and fixed thereon. The heat store 2 would then not have a separate heat store housing 20, and, in this case, fixing can take place in a detachable and repeatably attachable manner on the actuator housing 10.

Figure 4:
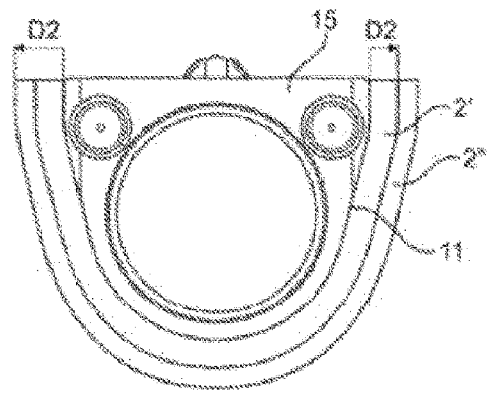
FIG. 4—shows a sectional illustration with two different heat storage media.

A further variant of this embodiment is shown in FIG. 4, in which only the actuator housing 10 with the actuator housing section 11, against which the respective variant of the heat store 2', 2" rests, is shown. In the exemplary embodiment illustrated, the respective heat store 2', 2" is arranged on the outer side of the actuator housing 10. FIG. 4 illustrates two variants of the heat store 2, the first variant with the heat store 2' consisting of a material containing salt or predominantly salt, in particular metastable salt. The second variant of the heat store 2" is formed from paraffin and has a greater thickness D2 than the first variant of the heat store 2' with a first thickness D1. This is due to the fact that the enthalpy of the salt and its density is greater than that of paraffin and thus, by comparison, less volume of heat storage medium 26 is required. Both heat stores 2', 2" rest against the actuator housing section 11, which is provided for heat exchange or heat transfer from the actuator housing 10 to the heat store 2', 2".

If the respective heat storage medium 26 of the heat store 2', 2" is not dimensionally stable, it is possible, instead of forming the heat store 2', 2" from the respective heat storage medium 26, to arrange around it a corresponding shell, which serves as a heat store housing and forms a cavity in which the respective heat storage medium is arranged. Particularly in the case of an arrangement having a flexible heat store housing, or at least a partially flexible heat store housing, it is possible to use a deformable heat storage medium which is applied to the actuator housing 10 in a deformable state and is then solidified or crystallized. This facilitates close and full-surface contact in the region of the outer side of the actuator housing 10 which is provided for heat transfer.

Figure 5:
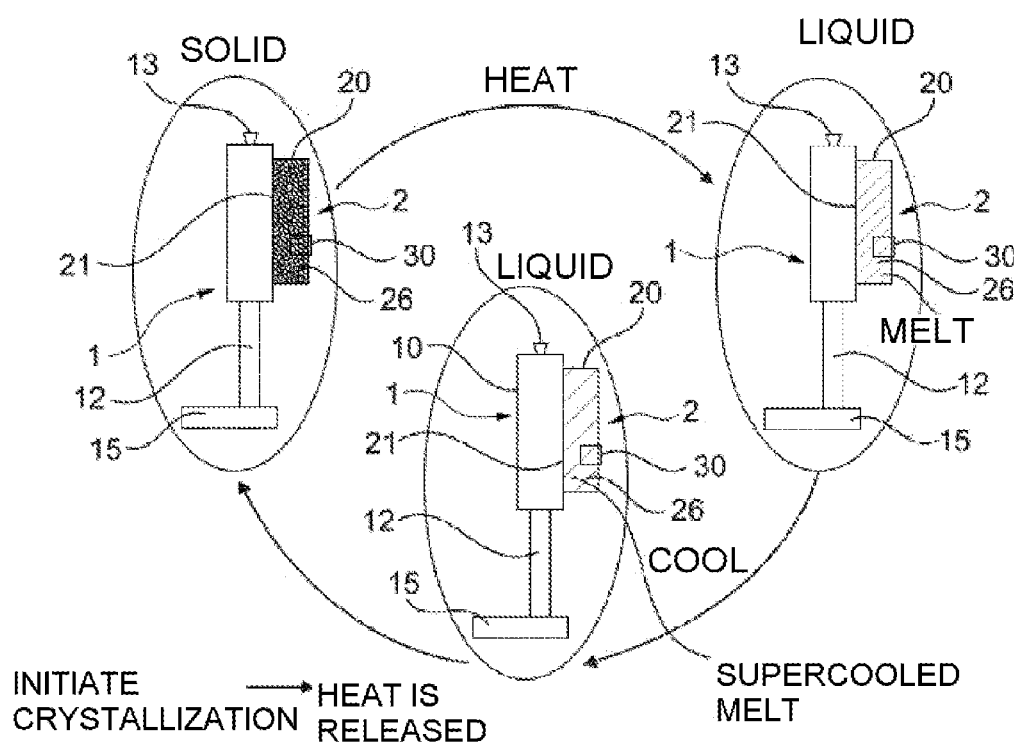
FIG. 5—shows a schematic illustration of the use of the invention.

FIG. 5 shows a variant of the invention in which the actuator 1 is designed as part of an orthopedic device. A pyramid adapter 13 is arranged on the upper end of the actuator housing 10 in order to connect the actuator 1 to, for example, an upper part of a leg orthosis or prosthesis. The piston rod 12 projects from the actuator housing 10 and leads to a lower part 15 of the orthopedic device. The heat store 2 with a heat store housing 20 is arranged on the outer side of the actuator housing 10. In the illustration on the left, the heat storage medium 26 is arranged in a solid state inside the heat store housing 2, on the receiving region 21 of the actuator housing 10. If, for example, frictional energy is then converted into heat or electrical energy is dissipated into heat by actuation of the actuator 1, this thermal energy is stored both in the actuator 1 and in the heat store 2. As a result, the maximum operating time of the actuator 1 and thus also of the orthopedic device is extended since the actuators have a maximum operating temperature which must not be exceeded. If, for example, an actuator temperature of 80° C. is reached, the user must wait until the thermal energy has been released to the environment and the joint or the orthopedic device has cooled sufficiently. With the heat store 2 arranged on the receiving region 21, it is possible to absorb the thermal energy and store it in the heat storage medium in order then to release the absorbed energy at another, definable time, for example during a rest phase. The user therefore no longer has to wait until the joint can be used again, or else the joint or the orthopedic device can be used for a longer period of time with the same cooling time. The heat store is preferably fixed on the actuator in such a way that it can be removed in a simple manner and can be fitted again in a simple manner. In particular, the heat store can be fixed to and removed from the actuator without tools, thus enabling a user to change, in particular extend, the heat storage capacity and thus the operating time of the actuator.

The removed heat store can cool down, while the newly arranged substitute heat store can absorb heat from the actuator housing.

The right-hand illustration shows the state of the heat store 2 which is assumed when heat is stored in the heat store 2. The heat storage medium 26 has melted and accordingly is liquid or of low viscosity. Thermal energy from the actuator 1 is absorbed in the heat storage medium 26 of the heat store 2. At a later time, the heat store 2 and, where applicable, also the actuator 1 are then cooled, this being shown in the central, lower figure. The heat storage medium 26 within the heat store 2 is initiated with a freely selectable event, which is, if appropriate, manually triggered by a trigger signal. If, for example, a metastable salt is used, there is the possibility of defining the time when the thermal energy is to be released again. If the orthopedic device or the joint or actuator 1 overheats, it is no longer absolutely necessary to wait until all the thermal energy has been released to the environment before the actuator can be used again. On the contrary, the energy is stored in a chemical reaction and can be released at any time. The waiting time until a joint or an orthopedic device is ready for use again after overheating is thereby shortened. Particularly in the case of a rapidly exchangeable heat store 2, the service life can thus be greatly extended. The energy of entropy is not automatically released by the salt or metastable salt as the heat storage medium; on the contrary, only the energy of the specific heat capacity of the actuator 1 has to be released. The cooling time is thereby considerably shortened. The remaining energy of entropy can be released at any desired, specifiable time. Until recrystallization is initiated, the joint can continue to release the energy at the level of the specific heat capacity of the orthopedic device or of the actuator 1. Once the thermal energy has been released from the heat store 2, the state on the left in FIG. 5 is established.

The recrystallization of a salt can be initiated, for example, by a pressure wave, for example by actuation of a metal plate or else by a vibration motor or by switching on another trigger or trigger mechanism 30. The trigger mechanism 30 is illustrated schematically in FIG. 5 and can be arranged directly on the heat store 2 so as to be accessible from the outside. For example, a button, a switch or a flexible location can be formed on the heat store housing, by means of which the metal plate or some other actuator can be activated in order to trigger a pressure wave by means of which the crystallization of the heat storage medium 26 can take place at the respectively desired time. By using a latent heat store in the form of a salt, it is possible to provide a comparatively lightweight heat store with a small volume. Compared with paraffin, the enthalpy of salt is greater, but the heat capacity is lower.

Figure 6:
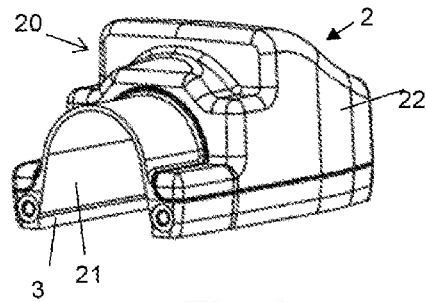
FIG. 6—shows a perspective view of a heat store.

A further variant of the invention is illustrated in FIG. 6, in which the heat store 2 is illustrated with an outer wall 22 and a receiving region 21. The actual actuator is not illustrated and can be designed as a damper or as a motor drive. Together with the outer wall 22, the receiving region 21 forms a cavity and thus, overall, a heat store housing 20 which advantageously has a heat storage medium and is, in particular, filled therewith. The heat storage medium is, for example, wax or some other heat storage material with which it is possible to dissipate and absorb thermal energy from the actuator via the receiving region 21. A projection or a positive engagement element is arranged or formed on the receiving region 21 as a fastening device 3 for fixing to the actuator (not illustrated). A correspondingly shaped positive engagement element is arranged or formed in the actuator. Other forms of positive engagement elements such as hook-and-loop fasteners, clips, undercuts, screws or the like can be used as fastening devices 3. Instead of a positive engagement element, the fastening device 3 can also be designed as a magnet or clamping element in order to allow nonpositive fastening.

Figure 7:
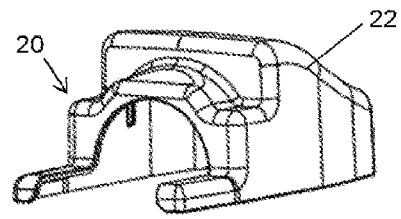
FIG. 7—shows a heat store according to FIG. 6 without a receiving region.

In FIG. 7, the heat store 2 is illustrated without the receiving region 21, which can be designed, for example, as a conductive metal. A heat conductor or a heat-conducting coating can be formed or arranged on the underside of the receiving region 21 or on the side of the receiving region which faces the actuator in order to facilitate or allow heat transfer from the actuator to the heat store 2. Within the heat store housing 20, which can be adhesively bonded to the receiving region 21 or fixed thereon in some other way, a cavity is formed, which will be explained in greater detail with reference to FIG. 8. The heat store housing 20 with the outer wall 22 is closed toward the receiving region 21, and therefore the heat store housing 20 can be designed as an independent module which is subsequently fixed on the receiving region 21.

Figure 8:
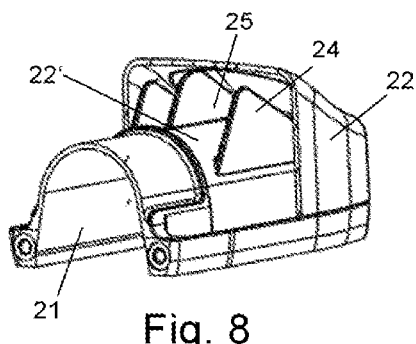
FIG. 8—shows an illustration of FIG. 6 with a partially sectioned outer wall.

A partially sectioned illustration of the heat store housing 20 mounted on the receiving region 21 is illustrated in FIG. 8. Together with the inner wall 22', the outer wall 22 forms the cavity 25 in which the heat storage medium 24 can be arranged. In the illustrated exemplary embodiment, three dividing elements 24 extend from the inner wall 22' in the direction of the outer wall 22, and, in the illustrated exemplary embodiment, extend parallel upward away from the receiving section 21, with the result that a total of four compartments is formed within the cavity 25. The compartments are connected to one another, and therefore heat exchange and possibly material exchange can take place in the case of a liquefied heat storage medium.

Figure 9:
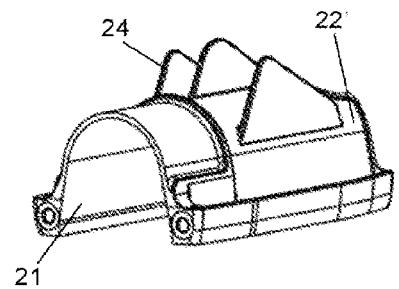
FIG. 9—shows a view of FIG. 8 without the outer wall.

FIG. 9 shows the arrangement with the receiving region 21 and the heat store housing 20 without the outer wall but with the inner wall 22' and the dividing walls 24 projecting upwards therefrom. The dividing walls 24 can be formed in one piece with the inner wall 22'; alternatively, the dividing walls 24 can be arranged subsequently on the inner wall 22' and fastened thereon.

Figure 10:
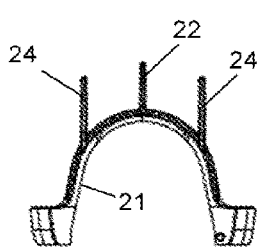
FIG. 10—shows a side view of FIG. 9.

FIG. 10 shows the view according to FIG. 9 in a side view. It can be seen from FIG. 10 that the inner wall 22' does not extend over the entire receiving region 21, but that a cutout is left free which is not covered over by the heat store 2. In principle, it is possible to cover over the entire area of this region as well and to cover it with the heat store 2.

Figure 11:
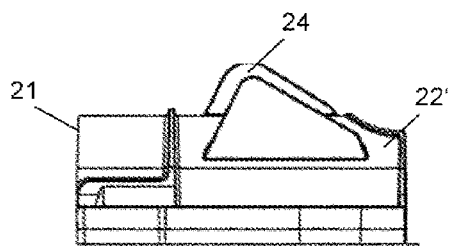
FIG. 11—shows a frontal view of FIG. 10.

The view according to FIG. 11 shows the parallel alignment of the three dividing walls 24 and the substantially vertically upward orientation.

Figure 12:
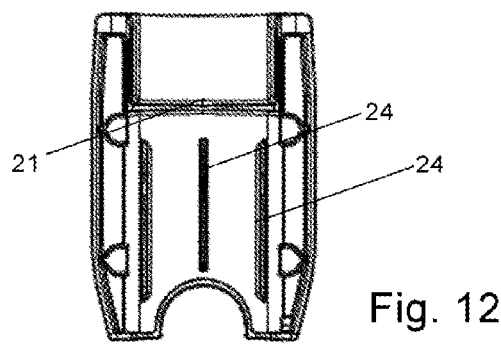
FIG. 12—shows a plan view of FIG. 11.

The plan view in FIG. 12 shows the cutout in the front region of the heat store housing 20, in which the receiving region 21 is not covered over by the heat store housing 20 and the inner wall 22'.

In addition to a subdivision function and separation of individual chambers, the dividing elements 24 also have other functions, namely the stabilization of the heat store 2 and heat conduction from the receiving region 21 and the inner wall 22' into the interior of the heat store 2. The heat storage medium arranged in the cavity 25 is heated more uniformly by the dividing elements 24 which project into the cavity 25 than if heat conduction were to take place only via the walls. For this purpose, the dividing elements 24 can consist of a material which has a good thermal conductivity, for example of a material which has a thermal conductivity of the receiving region 21. By virtue of the transfer of heat via the dividing elements 24, the heat storage medium in the cavity 25 is heated more uniformly. In addition to the edge zones, heat is also applied to the core of the cavity 25, thereby enabling improved heat dissipation from the actuator to take place.

The invention claimed is:

1. An actuator for an orthopedic device, the actuator comprising:
   an actuator housing; and
   a heat store for storing heat produced during operation of the actuator;
   wherein the heat store has a heat store housing comprising an outer wall comprising a rigid, dimensionally stable material, the outer wall of the heat store housing defines and encloses a cavity configured to contain a heat storage medium therein;
   wherein the heat store comprises a receiving region and is configured to be detachably fastened to the actuator housing, wherein a shape of the receiving region is configured to correspond to an actuator housing section and, in an installed state of the heat store, the receiving region is in heat-transferring contact with the actuator housing section.

2. The actuator as claimed in claim 1, wherein the heat store is nonpositively and/or positively fastened to the actuator housing.

3. The actuator as claimed in claim 1, wherein fastening devices are arranged or formed on the heat store and the actuator housing, wherein the fastening devices comprise at least one of screw sockets, undercuts, clips, clamping elements, plugs, plug receptacles, magnets, ferromagnetic elements, and/or hook-and-loop fastening elements.

4. The actuator as claimed in claim 1, wherein positive engagement elements are arranged or formed on a side of the receiving region which faces the actuator, said positive engagement elements being designed to correspond to positive engagement elements on an outer side of the actuator housing.

5. The actuator as claimed in claim 1, wherein the heat store is designed to be at least partially flexible on a side of the receiving region which faces the actuator.

6. The actuator as claimed in claim 1, wherein the heat store is designed to be at least partially rigid on a side which faces away from the actuator.

7. The actuator as claimed in claim 1, wherein the heat store is formed from different materials, and the material in the receiving region has a thermal conductivity Ami which is higher than the thermal conductivity AM2 of a second material outside the receiving region.

8. The actuator as claimed in claim 1, wherein an outer contour of a side of the heat store which faces away from the actuator and/or a contour of the receiving region have/has a contour which is designed to correspond to a contour of the outer side of the actuator housing.

9. The actuator as claimed in claim 1, wherein at least one heat conductor is arranged between the actuator housing and the heat store, wherein the at least one heat conductor comprises a thermal paste, a heat- conducting mat, and/or a heat-conducting plate.

10. The actuator as claimed in claim 1, wherein it is designed as a hydraulic actuator.

11. The actuator as claimed in claim 1, wherein the heat store surrounds the actuator housing circumferentially.

12. The actuator as claimed in claim 1, wherein the heat store is of multi-part design.

13. The actuator as claimed in claim 1, wherein the heat storage medium has a specific heat capacity of at least $c_p=1$ J/(g*K) at a temperature of T=25° C.

14. The actuator as claimed in claim 1 wherein the heat storage medium has a specific enthalpy of fusion of at least $h_{WM}=100$ kJ/kg.

15. The actuator as claimed in claim 1, wherein the specific heat capacity of the heat storage medium is higher than the specific heat capacity of the actuator housing.

16. The actuator as claimed in claim 1, wherein the heat storage medium is in the form of a wax, paraffin, a salt, salt hydrate, metastable salt hydrate, sodium acetate trihydrate, or a dimensionally stable silica gel.

17. The actuator as claimed in claim 1, wherein the heat storage medium is designed to be actively triggerable.

18. An orthopedic device having an actuator as claimed in claim 1.

19. A heat store having a heat store housing as claimed in claim 1 for fastening on an actuator of an orthopedic device.

20. An actuator for an orthopedic device, the actuator comprising:

an actuator housing; and a heat store for storing heat produced during operation of the actuator, wherein the heat store has a heat store housing comprising an outer wall comprising a rigid, dimensionally stable material, the outer wall of the heat store housing defines and encloses a cavity configured to contain a heat storage medium therein; and wherein the heat store is configured to be detachably fixed on or in the actuator housing by a fastening device, and wherein the heat store comprises a receiving region, wherein a shape of the receiving region is configured to correspond to an actuator housing section and, in an installed state of the heat store, the receiving region is in heat-transferring contact with the actuator housing section.

* * * * *